(12) United States Patent
Wang et al.

(10) Patent No.: US 11,744,833 B2
(45) Date of Patent: *Sep. 5, 2023

(54) PHARMACEUTICAL COMPOSITIONS AND METHODS FOR TREATMENT OF INSOMNIA

(71) Applicant: LA PharmaTech Inc., Blacksburg, VA (US)

(72) Inventors: Jianmin Wang, Blacksburg, VA (US); Fengyuan Jia, Beijing (CN)

(73) Assignee: LA PharmaTech Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/673,136

(22) Filed: Feb. 16, 2022

(65) Prior Publication Data

US 2022/0168318 A1 Jun. 2, 2022

Related U.S. Application Data

(63) Continuation-in-part of application No. 16/884,459, filed on May 27, 2020, which is a continuation-in-part of application No. 16/382,885, filed on Apr. 12, 2019, now Pat. No. 10,966,989.

(51) Int. Cl.
*A61K 31/55* (2006.01)
*A61K 31/4045* (2006.01)
*A61P 25/20* (2006.01)

(52) U.S. Cl.
CPC .......... *A61K 31/55* (2013.01); *A61K 31/4045* (2013.01); *A61P 25/20* (2018.01)

(58) Field of Classification Search
None
See application file for complete search history.

(56) References Cited

U.S. PATENT DOCUMENTS

| | | | |
|---|---|---|---|
| 4,871,733 A * | 10/1989 | Sunshine | A61K 31/44 514/315 |
| 5,068,233 A | 11/1991 | Achterrath-Tuckerman et al. | |
| 5,086,050 A | 2/1992 | Hettche et al. | |
| 5,110,814 A | 5/1992 | Engel et al. | |
| 5,430,029 A | 7/1995 | Biella et al. | |
| 5,958,964 A * | 9/1999 | Pappolla | A61K 31/4045 514/415 |
| 5,994,357 A | 11/1999 | Theoharides | |
| 6,008,221 A | 12/1999 | Smith et al. | |
| 6,017,909 A | 1/2000 | Hettche et al. | |
| 6,191,133 B1 | 2/2001 | Coppen | |
| 6,200,607 B1 | 3/2001 | Bridgeman | |
| 6,849,621 B2 | 2/2005 | Rosenblum et al. | |
| 7,022,687 B1 | 4/2006 | Szelenyi et al. | |
| 7,220,735 B2 | 5/2007 | Ting et al. | |
| 7,355,042 B2 | 4/2008 | Edgar et al. | |
| 7,384,981 B2 | 6/2008 | Kiliaan et al. | |
| 7,615,550 B2 | 11/2009 | Heightman et al. | |
| 7,786,161 B2 | 8/2010 | Tani et al. | |
| 7,888,391 B2 | 2/2011 | Kiliaan et al. | |
| 8,071,073 B2 | 12/2011 | Dang et al. | |
| 8,168,620 B2 | 5/2012 | Lulla et al. | |
| 8,304,405 B2 | 11/2012 | Lulla et al. | |
| 8,318,709 B2 | 11/2012 | Lulla et al. | |
| 8,362,078 B2 | 1/2013 | Kiliaan et al. | |
| 8,372,451 B2 | 2/2013 | Vuckovic | |
| 8,440,243 B2 | 5/2013 | Maewal | |
| 8,518,919 B2 | 8/2013 | Dang et al. | |
| 8,741,319 B2 | 6/2014 | Crain et al. | |
| 8,758,816 B2 | 6/2014 | Fuge et al. | |
| 8,859,531 B2 | 10/2014 | Lee et al. | |
| 8,865,733 B2 | 10/2014 | Felder | |
| 9,119,846 B2 * | 9/2015 | Zisapel | A61K 31/465 |
| 9,278,092 B2 | 3/2016 | Chase et al. | |
| 9,308,223 B2 | 4/2016 | Maewal | |
| 9,504,712 B2 | 11/2016 | Kiliaan et al. | |
| 9,662,359 B2 | 5/2017 | Vuckovic | |
| 9,700,548 B2 * | 7/2017 | Knutsen | A61K 31/56 |
| 9,844,525 B2 | 12/2017 | Kiliaan et al. | |
| 9,901,585 B2 | 2/2018 | Lulla et al. | |
| 9,919,050 B2 | 3/2018 | Dang et al. | |
| 10,045,915 B2 | 8/2018 | Glenn, Jr. et al. | |
| 10,639,314 B1 | 5/2020 | Wang et al. | |
| 10,639,315 B1 | 5/2020 | Wang et al. | |
| 10,639,316 B1 | 5/2020 | Wang et al. | |
| 10,682,343 B2 * | 6/2020 | Hand | A23L 33/10 |
| 10,898,493 B2 | 1/2021 | Wang et al. | |

(Continued)

FOREIGN PATENT DOCUMENTS

AU 2019443520 A1 12/2021
AU 2019445048 A1 12/2021

(Continued)

OTHER PUBLICATIONS

Hou, Ruihua and Baldwin, David S., "A neuroimmunological perspective on anxiety disorders", Human Psychopharmacol Clin Exp. 2012, vol. 27: 6-14.

Hou, Ruihua et al., "Peripheral inflammatory cytokines and immune balance in Generalized Anxiety Disorder: case-controlled study", Brain Behav Immun. May 2017; 62: 212-218.

Hua, S. "Advances in Nanoparticulate Drug Delivery Approaches for Sublingual and Buccal Administration". Nov. 10, 2019 (Article 1328), pp. 1-9.

Jeon, Sang Won and Kim, Yong Ku, "Detrimental effect of preservative in eye drops: Neuroinflammation and cytokine abnormality in major depression: Cause or consequence in that illness?" World Journal of Psychiatry, Sep. 22, 2016; 6(3): 283-293.

(Continued)

*Primary Examiner* — Leslie A. Royds Draper
(74) *Attorney, Agent, or Firm* — New River Valley IP Law, P.C.; Michele L. Mayberry

(57) ABSTRACT

Pharmaceutical compositions comprising azelastine or a pharmaceutically acceptable salt of azelastine and melatonin are disclosed. Methods of using the pharmaceutical compositions for treating patients suffering from insomnia are also disclosed.

1 Claim, No Drawings

(56) References Cited

U.S. PATENT DOCUMENTS

| | | | |
|---|---|---|---|
| 10,946,026 | B2 | 3/2021 | Wang et al. |
| 10,966,989 | B2 | 4/2021 | Wang et al. |
| 11,116,773 | B2 | 9/2021 | Wang et al. |
| 11,318,144 | B2 * | 5/2022 | Wang .................. A61K 31/714 |
| 11,351,179 | B1 | 6/2022 | Wang et al. |
| 11,389,458 | B2 | 7/2022 | Wang et al. |
| 11,690,849 | | 7/2023 | Wang et al. |
| 2003/0229030 | A1 | 12/2003 | Theoharides |
| 2005/0163843 | A1 | 7/2005 | Boehm et al. |
| 2006/0051416 | A1 | 3/2006 | Rastogi et al. |
| 2009/0318703 | A1 | 12/2009 | Tani et al. |
| 2010/0152108 | A1 | 6/2010 | Hung et al. |
| 2012/0237570 | A1 | 9/2012 | Crain et al. |
| 2013/0252929 | A1 | 9/2013 | Lee et al. |
| 2014/0127328 | A1 | 5/2014 | Crain et al. |
| 2014/0158117 | A1 | 6/2014 | Dang et al. |
| 2015/0216849 | A1 | 8/2015 | Dedhiya et al. |
| 2016/0166543 | A1 * | 6/2016 | Joshi .................. A61K 9/0095 514/357 |
| 2017/0035780 | A1 | 2/2017 | Lulla et al. |
| 2018/0104294 | A1 | 4/2018 | Vuckovic |
| 2018/0116979 | A1 | 5/2018 | Clarence-Smith et al. |
| 2020/0323867 | A1 | 10/2020 | Wang et al. |
| 2020/0323868 | A1 | 10/2020 | Wang et al. |
| 2020/0323870 | A1 | 10/2020 | Wang et al. |
| 2020/0323871 | A1 | 10/2020 | Wang et al. |
| 2020/0323873 | A1 | 10/2020 | Wang et al. |
| 2020/0323876 | A1 | 10/2020 | Wang et al. |
| 2020/0323877 | A1 | 10/2020 | Wang et al. |
| 2021/0069209 | A1 | 3/2021 | Wang et al. |
| 2022/0000882 | A1 | 1/2022 | Wang et al. |
| 2022/0096491 | A1 | 3/2022 | Wang et al. |
| 2023/0000882 | A1 | 1/2023 | Wang et al. |

FOREIGN PATENT DOCUMENTS

| | | | |
|---|---|---|---|
| AU | 2019446955 | A1 | 12/2021 |
| CA | 3136633 | A1 | 10/2020 |
| CA | 3137393 | A1 | 11/2020 |
| CA | 3139082 | A1 | 11/2020 |
| CN | 113924098 | A | 1/2022 |
| CN | 113939276 | A | 1/2022 |
| CN | 114072945 | A | 2/2022 |
| EP | 3952840 | A1 | 2/2022 |
| EP | 3962488 | A1 | 3/2022 |
| EP | 3973586 | A1 | 3/2022 |
| JP | 2012232978 | A | 11/2012 |
| JP | 2016529307 | A | 9/2016 |
| JP | 2019019113 | A | 2/2019 |
| JP | 2022535644 | A | 8/2022 |
| JP | 2022536017 | A | 8/2022 |
| JP | 2022539944 | A | 9/2022 |
| WO | WO-02056876 | A2 * | 7/2002 ............. A61K 31/00 |
| WO | 2006058022 | A1 | 6/2006 |
| WO | 2007061454 | A1 | 5/2007 |
| WO | 2014018563 | A3 | 5/2014 |
| WO | 2017151723 | A1 | 9/2017 |
| WO | 2020209872 | A1 | 10/2020 |
| WO | 2020222799 | A1 | 11/2020 |
| WO | 2020236159 | A1 | 11/2020 |
| WO | 2021242235 | A1 | 12/2021 |
| WO | 2021242297 | A1 | 12/2021 |
| WO | 2021262196 | A1 | 12/2021 |
| WO | 2023014361 | A1 | 2/2023 |

OTHER PUBLICATIONS

Jones, Patrice et al. "Folate and Inflammation—links between folate and features of inflammatory conditions", Journal of Nutrition & Intermediary Metabolism 18 (2019) 100104, 6 pages.

Kappelmann, N. et al., "Antidepressant activity of anti-cytokine treatment: a systematic review and meta-analysis of clinical trials of chronic inflammatory conditions", Molecular Psychiatry, 2018, vol. 23, 335-313.

Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.

Kohler, Ole et al., "Inflammation in Depression and the Potential for Anti-Inflammatory Treatment." Current Neuropharmacology, 2016, 11, 732-712.

Kolb, Andreas F. and Petrie, Linda, "Folate deficiency enhances the inflammatory response of macrophages", Mol Immunol. Jun. 2013; 54(2):164-172.

Koo, Ja Wook et al., 2010, Nuclear factor-κB is a critical mediator of stress impaired neurogenesis and depressive behavior. PNAS, Feb. 9, 2010, vol. 107 (6) 2669-2674.

Leon, Michael, Sawmiller, Darrell, Shytle, R. Douglas, and Tan, Jun. 2018. Therapeutic Cocktail Approach for Treatment of Hyperhomocysteinemia in Alzheimer's Disease. Cell Med. 2018; 10: 2155179017722280.

Liu, Chun-Hong et al., Role of inflammation in depression relapse, Journal of Neuroinflammation (2019) 16:90, 11 pages.

Lv, Wei-jie et al., "Melatonin Alleviates Neuroinflammation and Metabolic Disorder in DSS-Induced Depression Rats". Oxidative Medicine and Cellular Longevity 2020, Article ID 1241894, 17 pages.

Maeng, Sung Ho and Hong, Heeok, "Inflammation as the Potential Basis in Depression." Int Neurourol J 2019; vol. 23(Suppl 2): S63-71.

Menendez Pelaez, A. and R. J. Reiter, "Distribution of melatonin in mammalian tissues: The relative importance of nuclear versus cytosolic localization". J. Pineal Res. 1993, 15: 59-69, 11 pages.

Munoz-Cano et al. "Severity of Allergic Rhinitis Impacts Sleep and Anxiety: Results from a Large Spanish Cohort". Clinical and Translational Allergy, 2018, 8 (Article 23), p. 1-9.

Naddafi, F., Mirshafiey A., The neglected role of histamine in Alzheimer's disease., Jun. 2013;28(4):327-36. doi: 10.1177/1533317513488925. Epub May 15, 2013.

Nadeem, R. et al., "Serum inflammatory markers in obstructive sleep apnea: a meta-analysis", Journal of Clinic Sleep Med Oct. 15, 2013; 9(10):1003-12, 10 pages.

Niazi, Sarfaraz K., Handbook of Pharmaceutical Manufacturing Formulations vols. 1-6, 2004, 304 pages.

Niraula, Anzela et al., "IL-6 Induced by Social Stress Promotes a Unique Transcriptional Signature in the Monocytes That Facilitate Anxiety." Biol Psychiatry 85 (8), 679-689, Apr. 15, 2019.

Patki, G. and Y.S. Lau, "Melatonin protects against neurobehavioral and mitochondrial deficits in a chronic mouse model of Parkinson's disease". Pharmacol. Biochem. Behav. 2011, 99: 704-711, 20 pages.

Reiter, R. J. et al., "Melatonin as an antioxidant: Under promises but over delivers". J. Pineal Res. 2016, 61: 253-278, 26 pages.

Reiter, R. J. et al., "Melatonin: Exceeding Expectations". Physiology 2014, 29: 325-333, 9 pages.

Reynolds, Edward, "Vitamin B12, folic acid, and the nervous system", The Lancet Neurology, Nov. 2006, Abstract, 35 pages.

Riethmuller et al. Arzneimittel-Forschung, 1994, vol. 44, No. 10, pp. 1136-1140.

Sedeyn, Jonathan Histamine Induces Alzheimer's Disease-Like Blood Brain Barrier Breach and local cellular Responses in Mouse Brain Organotypic Culture. Hindawi. Aug. 21, 2015.

Simons, F.E., Simons, K.J. Clinical pharmacology of new histamine H1 receptor antagonist. Clin Pharmacokinet. 1999;36:329-352.

Starkstein, et al., "The construct of generalized anxiety disorder in altheimer's disease," Am J Geriatr Psychiatry Jan. 2007 15(1) 42-49.

St-Jean, Genevieve; Turcotte, Isabelle; Bastien, Celyne H. Cerebral asymmetry in insomnia sufferers. Frontiers in Neurology 2012, 3, 1-12.

Szelenyi, I., Achterrath-Tuckermann, U., Schmidt, J., Minker, E., Paegelow, I., Werner, H. Azelastine: A multifaceted drug for asthma therapy. Agents Actions Suppl. 1991;34:295-311 (abstract).

(56) References Cited

OTHER PUBLICATIONS

Tanaka, Hibiki, Hashimoto, Mamoru, et al, 2015. Relationship Between Dementia Severity and Behavioural and Psychological Symptoms in Early-Onset Alzheimer's Disease. Psychogeriatrics. Dec. 2015;15(4):242-7.
Troubat, Romain et al., Neuroinflammation and Depression: A Review. Eur J Neurosci. Mar. 9, 2020 DOI: 10.1111/ejn.14720.
Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.
Yoneda, Kazunori, et al. 1997, Suppression by Azelastine Hydrochloride of NF-KB Activation Involved in Generation of Cytokines and Nitric Oxide. Japanese Journal of Pharmacology, 73: 145-53.
Zacny, James P., Paice, Judith A., and Coalson, Dennis W., 2012. Separate and combined psychopharmacological effects of alprazolam and oxycodone in healthy volunteers, Aug. 1, 2012; 124(3): 274-282.
Ciprandi, G., Pronzato, C., Passalacqua, G., et al. Topical azelastine reduces eosinophil activation and intercellular adhesion molecule-1 expression on nasal epithelial cells: An antiallergic activity. J Allergy Clin Immunol. 1996;98(6 Pt 1):1088-1096.
Conti, Pio et al., "Impact of Mast Cells in Depression Disorder: Inhibitory Effect of IL-37 (New Frontiers)". Immunol Res, vol. 66 (3), 323-331 Jun. 2018.
Co-Pending U.S. Appl. No. 16/382,885, Final office action dated Jun. 5, 2020, 13 pgs.
Co-Pending U.S. Appl. No. 16/382,885, Non-Final office action and list of references dated Nov. 29, 2019, 23 pgs.
Co-Pending U.S. Appl. No. 16/382,885, Non-Final office action dated Dec. 22, 2020, 19 pgs.
Co-Pending U.S. Appl. No. 16/382,885, Notice of Allowance dated Feb. 10, 2021, 9 pages.
Co-Pending U.S. Appl. No. 16/382,885, Response to Dec. 22, 2020 Non-Final office action filed Jan. 21, 2021, 7 pgs.
Co-Pending U.S. Appl. No. 16/382,885, Response to Jun. 5, 2020 Final office action filed Jul. 31, 2020, 9 pages.
Co-Pending U.S. Appl. No. 16/382,885, Response to Nov. 29, 2019 Non-Final office action filed Mar. 2, 2020.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Interview Summary dated Dec. 18, 2019, 7 pages.
Co-Pending U.S. Appl. No. 16/398,845, Non-Final Office Action dated Aug. 6, 2019, 25 pages.
Co-Pending U.S. Appl. No. 16/398,845, Notice of Allowance dated Jan. 21, 2020, 11 pages.
Co-Pending U.S. Appl. No. 16/398,845, Response to Non-Final Office Action dated Nov. 3, 2019, 9 pages.
Co-Pending U.S. Appl. No. 16/418,614, Interview Summary dated Dec. 18, 2019, 7 pages.
Co-Pending U.S. Appl. No. 16/418,614, Non-Final Office Action dated Aug. 6, 2019, 31 pages.
Co-Pending U.S. Appl. No. 16/418,614, Notice of Allowance dated Jan. 30, 2020, 12 pages.
Co-Pending U.S. Appl. No. 16/418,614, Response to Non-Final Office Action dated Nov. 3, 2019, 10 pages.
Co-Pending U.S. Appl. No. 16/424,788 Corrected Notice of Allowance, dated Jan. 7, 2021, 5 pages.
Co-Pending U.S. Appl. No. 16/424,788 Non-Final Office Action, dated Nov. 29, 2019, 24 pgs.
Co-Pending U.S. Appl. No. 16/424,788 Non-Final Office Action, dated Nov. 5, 2020, 8 pgs.
Co-Pending U.S. Appl. No. 16/424,788 Notice of Allowance, dated Dec. 17, 2020, 9 pages.
Co-Pending U.S. Appl. No. 16/424,788 Response to Nov. 29, 2019 Non-Final Office Action, filed Mar. 2, 2020.
Co-Pending U.S. Appl. No. 16/424,788 Response to Nov. 5, 2020 Non-Final Office Action, dated Dec. 2, 2020, 6 pages.
Co-Pending U.S. Appl. No. 16/424,788 Response to Restriction Requirement, dated Oct. 2, 2019, 3 pgs.
Co-Pending U.S. Appl. No. 16/424,788 Restriction Requirement, dated Aug. 9, 2019, 7 pgs.
Co-Pending U.S. Appl. No. 16/424,788, Final Office Action dated Aug. 28, 2020, 17 pages.
Co-Pending U.S. Appl. No. 16/424,788, Response to Aug. 28, 2020 Final Office Action filed Oct. 19, 2020, 6 pages.
Co-Pending U.S. Appl. No. 16/426,121, Interview Summary dated Dec. 18, 2019, 7 pages.
Co-Pending U.S. Appl. No. 16/426,121, Non-Final Office Action dated Aug. 6, 2019, 25 pages.
Co-Pending U.S. Appl. No. 16/426,121, Notice of allowance dated Jan. 21, 2020, 18 pages.
Co-Pending U.S. Appl. No. 16/426,121, Response to Non-Final Office Action dated Nov. 6, 2019, 9 pages.
Co-Pending U.S. Appl. No. 16/831,330, Non-Final Office Action dated Apr. 7, 2021, 16 pages.
Co-Pending U.S. Appl. No. 16/831,330, Notice of Allowance dated Aug. 3, 2021, 8 pages.
Co-Pending U.S. Appl. No. 16/831,330, Response to Apr. 7, 2021 Non-Final Office Action filed Jul. 21, 2021, 7 pages.
Co-Pending U.S. Appl. No. 16/834,146, Final Office Action dated Mar. 18, 2022, 20 pages.
Co-Pending U.S. Appl. No. 16/834,146, Non-Final Office Action dated Nov. 15, 2021, 29 pages.
Co-Pending U.S. Appl. No. 16/834,146, Response to Nov. 15, 2021 Non-Final Office Action, dated Feb. 22, 2022, 9 pages.
Co-Pending U.S. Appl. No. 16/884,459, Final Office Action dated Dec. 10, 2021, 19 pages.
Co-Pending U.S. Appl. No. 16/884,459, Final Office Action dated Dec. 15, 2020, 15 pages.
Co-Pending U.S. Appl. No. 16/884,459, Non-Final Office Action dated Aug. 11, 2020, 35 pages.
Co-Pending U.S. Appl. No. 16/884,459, Non-Final Office Action dated Sep. 14, 2021, 35 pages.
Co-Pending U.S. Appl. No. 16/884,459, Response to Aug. 11, 2020 Non-Final Office Action dated Nov. 12, 2020, 11 pages.
Co-Pending U.S. Appl. No. 16/884,459, Response to Dec. 15, 2020 Final Office Action, filed Mar. 15, 2021, 30 pages.
Co-Pending U.S. Appl. No. 16/884,459, Response to Dec. 10, 2021 Final Office Action, filed Feb. 25, 2022, 18 pages.
Co-Pending U.S. Appl. No. 16/884,459, Response to Sep. 14, 2021 Non-Final Office Action, filed Nov. 16, 2021, 9 pages.
Co-Pending U.S. Appl. No. 16/884,459, Rule 132 Declaration dated Feb. 24, 2022, 4 pages.
Co-Pending U.S. Appl. No. 16/884,553, Non-Final Office Action dated Aug. 11, 2020, 26 pages.
Co-Pending U.S. Appl. No. 16/884,553, Notice of Allowance dated Dec. 2, 2020, 9 pages.
Co-Pending U.S. Appl. No. 16/884,553, Response to Aug. 11, 2020 Non-Final Office Action dated Nov. 12, 2020, 8 pages.
Co-Pending U.S. Appl. No. 16/913,927, Final Office Action dated Dec. 3, 2021, 12 pages.
Co-Pending U.S. Appl. No. 16/913,927, Final Office Action dated Jun. 2, 2021, 16 pages.
Co-Pending U.S. Appl. No. 16/913,927, Non-Final Office Action dated Aug. 11, 2021, 17 pages.
Co-Pending U.S. Appl. No. 16/913,927, Non-Final Office Action dated Feb. 19, 2021, 19 pages.
Co-Pending U.S. Appl. No. 16/913,927, Non-Final Office Action dated Nov. 9, 2020, 24 pages.
Co-Pending U.S. Appl. No. 16/913,927, Notice of Allowance dated Mar. 21, 2022, 11 pages.
Co-Pending U.S. Appl. No. 16/913,927, Response to Aug. 11, 2021 Non-Final Office Action, dated Nov. 10, 2021, 6 pages.
Co-Pending U.S. Appl. No. 16/913,927, Response to Aug. 27, 2020 Restriction Requirement, filed Oct. 20, 2020, 5 pages.
Co-Pending U.S. Appl. No. 16/913,927, Response to Dec. 3, 2021 Final Office Action, dated Mar. 3, 2022, 3 pages.

(56) References Cited

OTHER PUBLICATIONS

Co-Pending U.S. Appl. No. 16/913,927, Response to Feb. 19, 2021 Non-Final Office Action filed May 19, 2021, 10 pages.
Co-Pending U.S. Appl. No. 16/913,927, Response to Jun. 2, 2021 Final Office Action, dated Jul. 30, 2021, 6 pages.
Co-Pending U.S. Appl. No. 16/913,927, Response to Nov. 9, 2020 Non-Final Office Action filed Feb. 5, 2021, 8 pages.
Co-Pending U.S. Appl. No. 16/913,927, Restriction Requirement dated Aug. 27, 2020, 5 pages.
Co-Pending U.S. Appl. No. 17/094,405, Final Office Action dated Jul. 30, 2021, 22 pages.
Co-Pending U.S. Appl. No. 17/094,405, Non-Final Office Action dated Apr. 14, 2021, 21 pages.
Co-Pending U.S. Appl. No. 17/094,405, Response to Apr. 14, 2021 Non-Final Office Action filed Jul. 14, 2021, 7 pages.
Co-Pending U.S. Appl. No. 17/094,405, Response to Jan. 26, 2021 Restriction Requirement, filed Apr. 5, 2021, 7 pages.
Co-Pending U.S. Appl. No. 17/094,405, Response to Jul. 30, 2021 Final Office Action, dated Sep. 30, 2021, 10 pages.
Co-Pending U.S. Appl. No. 17/094,405, Restriction Requirement dated Jan. 26, 2021, 5 pages.
Co-Pending U.S. Appl. No. 17/394,898, Examiner-Initiated Interview Summary for Interview dated Mar. 4, 2022, 1 page.
Co-Pending U.S. Appl. No. 17/394,898, Non-Final Office Action dated Nov. 24, 2021, 9 pages.
Co-Pending U.S. Appl. No. 17/394,898, Notice of Allowance and Examiner's Amendment dated Mar. 17, 2022, 13 pages.
Co-Pending U.S. Appl. No. 17/394,898, Response to Nov. 24, 2021 Non-Final Office Action, dated Feb. 23, 2022, 9 pages.
Co-Pending U.S. Appl. No. 17/394,898, Response to Oct. 21, 2021 Restriction Requirement, dated Nov. 10, 2021, 2 pages.
Co-Pending U.S. Appl. No. 17/394,898, Restriction Requirement dated Oct. 21, 2021, 9 pages.
Co-Pending U.S. Appl. No. 17/459,868, Preliminary Amendment, filed Aug. 27, 2021, 8 pages.
Co-Pending application No. PCT/US19/29885 International Search Report and Written Opinion dated Jul. 15, 2019. 7 pages.
Co-Pending application No. PCT/US19/33359 International Search Report and Written Opinion dated Aug. 15, 2019. 9 pages.
Co-Pending Application No. PCT/US20/34735, International Search Report and Written Opinion dated Aug. 17, 2020, 10 pages.
Co-Pending Application No. PCT/US20/39916, International Search Report and Written Opinion dated Oct. 8, 2020, 8 pages.
Co-Pending Application No. PCT/US20/59846, International Search Report and Written Opinion dated Mar. 8, 2021, 8 pages.
Co-Pending Application No. PCT/US2019/027293, Corrected Written Opinion, dated Oct. 29, 2019, 5 pages.
Co-Pending Application No. PCT/US2019/027293, Search Report & Written Opinion, dated Sep. 17, 2019, 8 pages.
Co-Pending Application No. PCT/US21/44654, International Search Report and Written Opinion, dated Nov. 15, 2021, 10 pages.
Co-Pending China National Stage Application No. 201980095322. X, English Version of Amended Claims as filed Oct. 11, 2021, 3 pages.
Cummings et al. "Effect of Dextromethorphan-Quinidine on Agitation in Patients with Alzheimer Disease Dimentia: A Randomized Clinical Trial". JAMA, 2015; 314(12):1242-1254.
eHealthMe.com "Azelastine and Xanax drug interactions—a phase IV clinical study of FDA data", dated Jan. 7, 2021, 5 pages.
Feng, Dan et al. "Folic acid inhibits lipopolysaccharide-induced inflammatory response in RAW264.7 macrophages by suppressing MAPKs and NF-kB activation", Inflamm Res. Sep. 2011;60(9):817-822.
Gaines, J. et al., "Inflammation mediates the association between visceral adiposity and obstructive sleep apnea in adolescents" Am J. Physiol. Endocrinol Metab., Nov. 1, 2016; 311(5), 8 pages.
Galatowicz, G., Ajayi Y, Stem ME, Calder VL. Ocular antiallergic compounds selectively inhibit human mast cell cytokines in vitro and conjunctival cell infiltration in vivo. Clin Exp Allergy. 2007; 37:1648-1656.

Georgin-Lavialle, S. et al., "Mast Cells' Involvement in Inflammation Pathways Linked to Depression: Evidence in Mastocytosis." Mol Psychiatry. 21 (11), 1511-1516 Nov. 2016.
Goedert, M., Spillantini, M.G,. 2006. A century of Alzheimer's disease. Science, 314:777-81.
Guignet, Michelle et al., "Persistent behavior deficits, neuroinflammation, and oxidative stress in a rat model of acute organophosphate intoxication", vol. 133, Jan. 2020, 101131.
Hansen et al. Clinical Interventions in Aging 2008, vol. 3, No. 2, pp. 211-225.
Hardeland, R., "Neurobiology, pathophysiology, and treatment of melatonin deficiency and dysfunction". The Scientific World Journal 2012, Article ID 640389, 19 pages.
Hashiro et al. "A Combination Therapy of Psychotropic Drugs and Antihistaminics or Antiallergics in Patients with Chronic Urticaria". Journal of Dermatological Sciences, 1996; 11:209-213.
Hatakeyama, Aiko, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).
Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.
Horak, Friedrich, "Effectiveness of twice daily azelastine nasal spray in patients with seasonal allergic rhinitis," Ther. Clin. Risk Manag., Oct. 2008; 4(5): 1009-1022.
(Wang, Jianmin) Co-Pending U.S. Appl. No. 16/382,885, filed Apr. 12, 2019, Specification and claims.
(Wang, Jianmin) Co-Pending U.S. Appl. No. 16/398,845, filed Apr. 30, 2019, Specification and Claims.
(Wang, Jianmin) Co-Pending U.S. Appl. No. 16/418,614, filed May 21, 2019, Specification and Claims.
(Wang, Jianmin) Co-pending U.S. Appl. No. 16/424,788, filed May 29, 2019, Specification and Claims.
(Wang, Jianmin) Co-Pending U.S. Appl. No. 16/426,121, filed May 30, 2019, Specification and Claims.
(Wang, Jianmin) Co-Pending U.S. Appl. No. 16/831,330, filed Mar. 26, 2020, Specification and Claims.
(Wang, Jianmin) Co-Pending U.S. Appl. No. 16/834,146, filed Mar. 30, 2020, Specification and Claims.
(Wang, Jianmin) Co-Pending U.S. Appl. No. 16/884,459, filed May 27, 2020, Specification and Claims.
(Wang, Jianmin) Co-Pending U.S. Appl. No. 16/884,553, filed May 27, 2020, Specification and Claims.
(Wang, Jianmin) Co-Pending U.S. Appl. No. 16/913,927, filed Jun. 26, 2020, Specification and Claims.
(Wang, Jianmin) Co-Pending U.S. Appl. No. 17/094,405, filed Nov. 10, 2020, Specification and Claims.
(Wang, Jianmin) Co-Pending U.S. Appl. No. 17/394,898, filed Aug. 5, 2021, Specification and Claims.
(Wang, Jianmin) Co-Pending U.S. Appl. No. 17/459,868, filed Aug. 27, 2021, Specification and Claims.
(Wang, Jianmin) Co-Pending U.S. Appl. No. 17/546,342, filed Dec. 9, 2021, Specification and Claims.
(Wang, Jianmin) Co-Pending Application No. PCT/US19/27293, filed Apr. 12, 2019, Specification and Claims.
(Wang, Jianmin) Co-Pending Application No. PCT/US19/29885, Filed Apr. 30, 2019, Specification and Claims.
(Wang, Jianmin) Co-Pending Application No. PCT/US19/33359, Filed May 21, 2019, Specification and Claims.
(Wang, Jianmin) Co-Pending Application No. PCT/US20/34735, filed May 27, 2020, Specification and Claims.
(Wang, Jianmin) Co-Pending Application No. PCT/US20/39916, Filed Jun. 26, 2020, Specification and Claims.
(Wang, Jianmin) Co-Pending Application No. PCT/US20/59846, filed Nov. 10, 2020, Specification and claims.
(Wang, Jianmin) Co-Pending Application No. PCT/US21/44654, filed Aug. 5, 2021, Specification and Claims.
(Wang, Jianmin) Co-Pending Application No. PCT/US22/16545, filed Feb. 16, 2022, Specification and Claims.

(56) References Cited

OTHER PUBLICATIONS (Wang, Jianmin) Co-Pending Australia National Stage Application No. 2019443520, Effective Filing Date Apr. 30, 2019, Specification and Claims (See PCT/US19/29885, which published as WO 2020/222799, for Specification and Claims as filed).
(Wang, Jianmin) Co-Pending Australia National Stage Application No. 2019445048, Effective Filing Date Apr. 12, 2019, Specification and Claims (See PCT/US19/27293, which published as WO 2020/209872, for Specification and Claims as filed).
(Wang, Jianmin) Co-Pending Australia National Stage Application No. 2019446955, Effective Filing Date May 21, 2019, Specification and Claims (See PCT/US19/33359, which published as WO2020/236159, for Specification and Claims as filed).
(Wang, Jianmin) Co-Pending Canada National Stage Application No. 3,136,633, filed Oct. 8, 2021, Specification and Claims, 25 pages.
(Wang, Jianmin) Co-Pending Canada National Stage Application No. 3,137,393, Filed Oct. 19, 2021, Specification and Claims, 17 pages.
(Wang, Jianmin) Co-Pending Canada National Stage Application No. 3,139,082, Filed Nov. 3, 2021, Claims and Amended Specification, 25 pages.
(Wang, Jianmin) Co-Pending China National Stage Application No. 201980095322.X, filed Oct. 11, 2021, Specification and Claims (32 pages) (see PCT/US19/27293, which published as WO2020/209872 for English Translation).
(Wang, Jianmin) Co-Pending China National Stage Application No. 201980095741.3, Filed Oct. 25, 2021, Specification and Amended Claims as filed (26 pages) with English Translation of the Amended Claims (2 pages) (See PCT/US19/29885, which published as WO 2020/222799, for English Translation of the Specification).
(Wang, Jianmin) Co-Pending China National Stage Application No. 201980096574.4, Filed Nov. 18, 2021, Specification and Amended Claims as filed (48 pages) with English Translation of the Amended Claims (4 pages) (See PCT/US19/33359, which published as WO2020/236159, for English Translation of the Specification).
(Wang, Jianmin) Co-Pending European National Stage Application No. 19924315.5, filed Nov. 11, 2021, Specification and Amended Claims as filed (34 pages).
(Wang, Jianmin) Co-Pending European National Stage Application No. 19927207.1, filed Nov. 29, 2021, Specification and Amended Claims as filed (26 pages).
(Wang, Jianmin) Co-Pending European National Stage Application No. 19929933.0, filed Dec. 21, 2021, Specification and Amended Claims as filed (35 pages).
(Wang, Jianmin) Co-Pending Japan National Stage Application No. 2021-556914, filed Sep. 17, 2021, Specification and Claims (19 pages) (see PCT/US19/27293, which published as WO 2020/209872, for English Translation).
(Wang, Jianmin) Co-Pending Japan National Stage Application No. 2021-558496, filed Sep. 21, 2021, Specification and Claims (15 pages) (See PCT/US19/29885, which published as WO 2020/222799, for English Translation).
(Wang, Jianmin) Co-Pending Japan National Stage Application No. 2021-566489, filed Nov. 9, 2021, Request for Entry and Specification and Claims (18 pages) (See PCT/US19/33359, which published as WO2020/236159, for English Translation of Specification and Claims).
Acuna-Castroviejo, D. et al., "Melatonin role in the mitochondrial function". Frontiers in Bioscience. 2007 12: 947-963, 17 pages.
Acuna-Castroviejo, D. et al., "Melatonin-mitochondria interplay in health and disease". Current Topics in Med. Chem. 2011; 11: 221-240, 20 pages.
Ancill et al. "Agitation in the Demented Elderly: A Role for Benzodiazepines?" International Clinical Psychopharmacology, 1991; 6:141-146.
Auld, F. et al., "Evidence for the efficacy of melatonin in the treatment of primary adult sleep disorders". Sleep Med. Rev. 2017, 34: 10-22, 39 pages.

Balashova, Olga A. et al. "Folate Action in Nervous System Development and Disease", Dev Neurobiol. Apr. 2018; 78(4): 391-402.
Bartlett, D. and Bear, M., "Rhinorrhea as a Result of Alzheimer's Disease Treatment: A Case Report", The Senior Care Pharmacist. Dec. 2019; 34(10):669-673, 5 pages.
Bennett, F. C. and Molofsky, A. V., "The immune system and psychiatric disease: a basic science perspective", Clinical and Experimental Immunology, 197: 291-307.
Bezprozvanny, Ilya. The rise and fall of Dimebon. National Institute of Health. Feb. 12, 2014.
Bottiglieri, Teodoro et al. "Homocysteine, folate, methylation, and monoamine metabolism in depression", J Neurol Neurosurg Psychiatry 2000; 69:228-232.
Bravo, Mónica de la Peña et al., "Inflammatory proteins in patients with obstructive sleep apnea with and without daytime sleepiness". Sleep Breath, Sep. 2007;11(3):177-85, Abstract only.
Casale, T. B. The interaction of azelastine with human lung histamine H1, beta, and muscarinic receptor-binding sites. J Allergy Clin Immunol. 1989;83:771-776.
Category H1 receptor antagonists. Wikipedia. Sep. 20, 2012.
Catena-Dell'osso, M. et al., 2011, Inflammatory and Neurodegenerative Pathways in Depression: A New Avenue for Antidepressant Development? Curr Med Chem. 18 (2), 245-55, Abstract, 2 pages.
"Donepezil—Medline Plus", Medline Plus, Dec. 15, 2017, 6 pages, [retrieved Dec. 19, 2022], https://medlineplus.gov/druginfo/meds/a697032.html.
"EPAR summary for the public", European Medicines Agency, Dec. 1, 2012, 3 pages, [retrieved Dec. 19, 2022], https://www.ema.europa.eu/en/documents/overview/prometax-epar-summary-public_en.pdf.
"Razadyne-galantamine hydrobromide tablet, film coated Rebel Distributors Corp", Dailymed, Nov. 11, 2010, 32 pages, [retrieved Dec. 19, 2022], https://dailymed.nlm.nih.gov/dailymed/drugInfo.cfm?setid=e62efb5a-d2cc-4e11-9e61-10e65ef3d897.
(Wang, Jianmin) Co-Pending U.S. Appl. No. 17/940,533, filed Sep. 8, 2022, Specification and Claims.
Co-Pending U.S. Appl. No. 16/834,146, Notice of Allowance dated Jun. 6, 2022, 8 pages.
Co-Pending U.S. Appl. No. 16/834,146, Response to Mar. 18, 2022 Final Office Action, dated May 12, 2022, 7 pages.
Co-Pending U.S. Appl. No. 16/884,459, Applicant-Initiated Interview Summary dated Apr. 5, 2022, 2 pages.
Co-Pending U.S. Appl. No. 16/884,459, Applicant-Initiated Interview Summary dated Jun. 24, 2022, 2 pages.
Co-Pending U.S. Appl. No. 16/884,459, Non-Final Office Action dated Aug. 30, 2022, 32 pages.
Co-Pending U.S. Appl. No. 16/884,459, Response to Aug. 30, 2022 Non-Final Office Action, filed Nov. 21, 2022, 12 pages.
Co-Pending U.S. Appl. No. 16/884,459, Rule 132 Declaration dated Nov. 18, 2022, 52 pages.
Co-Pending U.S. Appl. No. 17/094,405, Non-Final Office Action dated Apr. 14, 2022, 38 pages.
Co-Pending U.S. Appl. No. 17/940,533, Preliminary Amendment dated Sep. 8, 2022, 10 pages.
Co-Pending Application No. PCT/US22/16545, International Search Report and Written Opinion dated Jul. 7, 2022, 11 pages.
Co-Pending Application No. PCT/US22/16545, Invitation to Pay Fees dated Apr. 19, 2022, 2 pages.
Co-Pending European National Stage Application No. 19924315.5, Extended European Search Report dated Oct. 24, 2022, 6 pages.
Co-Pending European National Stage Application No. 19927207.1, Extended European Search Report dated Nov. 10, 2022, 10 pages.
Co-Pending European National Stage Application No. 19929933.0, Extended European Search Report dated Dec. 14, 2022, 11 pages.
Co-Pending Japan National Stage Application No. 2021-556914 Voluntary Amendment and Request for Exam dated Apr. 11, 2022, JP version (5 pages) and English (3 pages).
Co-Pending Japan National Stage Application No. 2021-558496 Voluntary Amendment and Request for Exam dated Apr. 14, 2022, JP version (4 pgs) and English (2 pgs).

(56) References Cited

OTHER PUBLICATIONS

Co-Pending Japan National Stage Application No. 2021-566489 Voluntary Amendment and Request for Exam dated May 17, 2022, JP version (5 pgs) and English (4 pgs).
Frisch, C. et al. "The histamine H1-antagonist chlorpheniramine facilitates learning in aged rats", Neuroscience Letters, vol. 229, No. 2, Jun. 27, 1997, pp. 89-92.
Tariot, P. N. et al. Memantine Treatment in Patients With Moderate to Severe Alzheimer Disease Already Receiving Donepezil, JAMA, Jan. 21, 2004, vol. 291, No. 3, p. 317-324, 8 pages.
(Wang, Jianmin) Co-Pending Canada National Stage Application No. 3,183,560, Filed Dec. 20, 2022, Claims and Specification (See WO2021/262196).
(Wang, Jianmin) Co-Pending China National Stage Application No. 202080102343.2, Filed Dec. 22, 2022, Specification and Amended Claims as filed (28 pages) with English Translation of the Amended Claims (3 pages) (See WO2021/262196, for English Translation of the Specification).
(Wang, Jianmin) Co-Pending European National Stage Application No. 20942038.9, filed Jan. 25, 2023, Specification and Amended Claims as filed (23 pages).
(Wang, Jianmin) Co-Pending Japan National Stage Application No. 2022-578962, filed Dec. 21, 2022, Specification and Claims (See WO2021/262196).
Co-Pending U.S. Appl. No. 17/940,533, Response to Jan. 9, 2023 Restriction Requirement, dated Jan. 24, 2023, 2 pages.
Co-Pending U.S. Appl. No. 17/940,533, Restriction Requirement dated Jan. 9, 2023, 5 pages.
Co-Pending China National Stage Application No. 201980095322. X, First Office Action (7 pages) dated Jan. 19, 2023 and English Translation (7 pages).
Beitz, Janice M. "Parkinson's disease: a review", Frontiers in Bioscience S6, 65-74, Jan. 1, 2014, 10 pages.
Co-Pending U.S. Appl. No. 16/884,459, Final Office Action dated Apr. 27, 2023, 20 pages.
Co-Pending U.S. Appl. No. 17/459,868, Non-Final Office Action dated Mar. 10, 2023, 18 pages.
Co-Pending U.S. Appl. No. 17/459,868, Response to Mar. 10, 2023 Non-Final Office Action, dated Mar. 22, 2023, 3 pages.
Co-Pending U.S. Appl. No. 17/940,533, Non-Final Office Action dated Mar. 9, 2023, 21 pages.
Co-Pending China National Stage Application No. 201980095741. 3, Office Action dated Mar. 23, 2023 (8 pages) and English Translation (9 pages).
Co-Pending Japan National Stage Application No. 2021-556914 Office Action dated Feb. 24, 2023 (4 pages) and English Translation (5 pages).
Co-Pending Japan National Stage Application No. 2021-556914 Voluntary Amendment and Request for Exam dated Apr. 11, 2022, JP version (5 pages) and English translation of the amended claims (4 pages).
Co-Pending Japan National Stage Application No. 2021-558496, Office Action dated Feb. 24, 2023 (3 pages) and English Translation (4 pages).
Co-Pending Japan National Stage Application No. 2021-566489, Office Action dated Mar. 29, 2023 (5 pages) and English Translation (7 pages).
Co-Pending Japan National Stage Application No. 2022-578962, Voluntary Amendment dated Feb. 24, 2023 (3 pages) with English Translation of the Amended Claims (3 pages).
Girard, J. et al. "Azelastine protects against CA1 traumatic neuronal injury in the hippocampal slice", European Journal of Pharmacology, vol. 300, Jan. 1, 1996, pp. 43-49.
Ljubenkov, Peter et al. "Dementia", Seminars in Neurology, 2016, vol. 36, No. 4, pp. 397-404.
Singh, Tanvir et al. "Alprazolam as a monotherapy for anxiety and depression", Psychiatry (Edgmont). Nov. 2005; 2(11):32, 1 page.
Sors, A. et al., "The Synergistic Enhancing-Memory Effect of Donepezil and S 38093 (a Histamine H3 Antagonist) Is Mediated by Increased Neural Activity in the Septo-hippocampal Circuitry in Middle-Aged Mice", Frontiers in Pharmacology, 2016, vol. 7, No. 492, pp. 1-12.
Co-Pending U.S. Appl. No. 17/940,533, Response to Mar. 9, 2023 Non-Final Office Action, dated Jun. 9, 2023, 8 pages.
Co-Pending European National Stage Application No. 19927207.1, Response to Nov. 10, 2022 Extended European Search Report, dated Jun. 9, 2023, 11 pages.
(Wang, Jianmin) Co-Pending U.S. Appl. No. 18/318,804, filed May 17, 2023, Specification and Claims.
Co-Pending China National Stage Application No. 201980095322. X, Response to Jan. 19, 2023 Office Action dated May 30, 2023 (7 pages) and English Translation of the amended claims (4 pages).
Co-Pending European National Stage Application No. 19924315.5, Response to Extended European Search Report, dated May 19, 2023, 6 pages.

\* cited by examiner

PHARMACEUTICAL COMPOSITIONS AND METHODS FOR TREATMENT OF INSOMNIA

CROSS-REFERENCE TO RELATED APPLICATIONS

The present application is a Continuation in Part application of U.S. patent application Ser. No. 16/884,459 filed on May 27, 2020, which application is a Continuation in Part application of U.S. patent application Ser. No. 16/382,885 filed on Apr. 12, 2019, the disclosure of which is hereby incorporated by reference herein in its entirety.

FIELD OF THE INVENTION

The invention relates to the field of practical medicine, namely, to the use of pharmaceutical compositions for treating, preventing, and/or alleviating manifestations of insomnia or symptoms thereof.

BACKGROUND OF THE INVENTION

Insomnia is often diagnosed through the presence of polysomnographic evidence of disturbed sleep, such as a long sleep latency, frequent nocturnal awakenings, or prolonged periods of wakefulness during the sleep period or even frequent transient arousals. Various population-based studies show that approximately 30-40% of a variety of adult samples drawn from different countries report one or more of the symptoms of insomnia: difficulty initiating sleep, difficulty maintaining sleep, waking up too early, and in some cases, nonrestorative or poor quality of sleep. Particularly, insomnia has a very negative impact on vulnerable patient groups, including active military personnel and veterans, patients with coexisting psychiatric and medical disorders, those in life transitions such as menopause, and elderly persons. Due to its chronicity, insomnia is associated with substantial impairments in an individual's quality of life such as a high rate of psychiatric comorbidities. Insomnia even poses a greater health risk due to the increased occurrence of daytime accidents.

Treatments for insomnia include benzodiazepine receptor agonists, such as triazolam, estazolam, zolpidem, zaleplon, eszopiclone, etc.; melatonin agonists, such as ramelteon; tricyclic antidepressants, such as doxepin; orexin receptor antagonists, such as suvorexant. These drugs do carry risks of tolerance, dependence, memory impairment, depression, headache, dizziness, somnolence, and so on.

Clinically, new treatments for insomnia are urgently needed that have significantly fewer side effects and can be provided to a wider range of patients experiencing insomnia who have additional medical or mental conditions.

Inflammation can be defined as one of the immune responses for protecting living organisms from damage. The immune system can be triggered by various factors such as pathogens, damage to cells, and stress that may induce acute or chronic inflammatory responses in organs including the brain, potentially leading to tissue damage or disease. The latest advancements in neurobiological research provide increasing evidence that inflammatory and neurodegenerative pathways play a relevant role in insomnia. Preclinical and clinical studies on insomnia highlighted an increased production of inflammatory markers, such as interleukin (IL)-1, IL-6, tumor necrosis factor (TNF)-α and interferon (INF)-α and γ, and overactivated inflammatory signaling pathways including nuclear factor kappa B (NF-κB). More recent studies have shown that blocking the biological actions of the cytokines IL-1 and TNF resulted in a reduction of physiological NREM sleep amount or NREM sleep rebound after sleep deprivation. On the other hand, increasing the availability of those cytokines promoted NREM sleep amount and intensity and suppressed REM sleep amount. These findings established both cytokines, IL-1 and TNF, as substances involved in the homeostatic regulation of sleep. Other cytokines, including IFN, IL-2, IL-4, IL-6, IL-10, IL-13, IL-15, and IL-18 also appear to have some sleep regulatory properties. The anti-inflammatory cytokines IL-4, IL-10, and IL-13 have been reported to attenuate NREM sleep amount in rabbits, while the pro-inflammatory acting cytokines IFN-γ, IL-2, IL-6, IL-15, and IL-18 have NREM sleep-promoting actions in animal models.

Azelastine is classified pharmacologically as a second-generation antihistamine and is a relatively selective, non-sedative, competitive antagonist at $H_1$ receptors for treatment of allergic rhinitis and asthma. But, more uniquely, its inhibition of inflammatory mediators and its mast cell stabilizing effects, in addition to its antihistaminic activity, place it among the new generation of dual-acting anti-inflammatory drugs. Its ability to modify several other mediators of inflammation, such as IL-1, IL-6, TNF-α and INF-α, and to reduce overactivation of the NF-κB inflammatory signaling pathway might contribute to its mechanism of action for potential treatment of insomnia. In vitro and in vivo studies, as well as clinical trials, support the dual effects of direct inhibition and stabilization of inflammatory cells. In vitro data indicate that azelastine's affinity for inhibition of mast cell degranulation may also decrease the release of other inflammatory mediators, including leukotrienes and interleukin-1β, among others. Preclinical studies show that azelastine also directly antagonizes other mediators of inflammation, such as tumor necrosis factor-α, leukotrienes, endothelin-1, and platelet-activating factor.

Melatonin is best known for its mediation of circannual variations in metabolism and reproductive competence in photosensitive species, its ability to influence circadian processes that are ubiquitous in organisms and in cells, and its sleep promoting activity. Each of these functions relies on the circadian message provided by the pineal-derived blood and cerebrospinal fluid melatonin rhythms. Melatonin is also highly effective as an antioxidant at the mitochondrial level and also an anti-inflammatory agent. The doses for membrane receptor-mediated circadian rhythm regulation are usually lower than those used for defeating free radicals, an action that is membrane receptor independent. High doses of melatonin are believed to be effective in alleviating overproduction of inflammatory markers, such as interleukin (IL)-1, IL-6, tumor necrosis factor (TNF)-α.

Therefore, a unique combination of azelastine (antihistamine agent with anti-inflammatory activities) with melatonin would potentially be, in terms of working through multi-mechanisms of actions, effective in the treatment of insomnia.

SUMMARY OF THE INVENTION

The present invention includes a pharmaceutical composition that comprises two active pharmaceutical ingredients. This pharmaceutical composition comprises the first active ingredient that is azelastine or a pharmaceutically acceptable salt of azelastine and the second active ingredient that is melatonin.

In some embodiments of this invention, the pharmaceutically acceptable salt of azelastine in the pharmaceutical composition is azelastine hydrochloride.

In some embodiments of this invention, azelastine hydrochloride (and/or other salt thereof) in the pharmaceutical composition is provided in an amount of about 2 mg to about 10 mg and melatonin in an amount of about 2 mg to about 20 mg.

The present invention also includes an oral pharmaceutical dosage form of the pharmaceutical composition that is a solid, liquid, gel, or solution form.

The present invention further includes use of the composition, such as by oral dosage, through administration to patients with insomnia.

In some embodiments of this invention, an oral pharmaceutical dosage form of the pharmaceutical composition containing azelastine hydrochloride (and/or other salt thereof) in an amount of about 2 mg to about 10 mg and melatonin in an amount of about 2 mg to about 20 mg is administered to patients with insomnia.

Embodiments include Aspect 1, which is a pharmaceutical composition, comprising: azelastine or a pharmaceutically acceptable salt of azelastine; melatonin; and one or more pharmaceutically acceptable excipients.

Aspect 2 is the pharmaceutical composition of Aspect 1, wherein the azelastine or the pharmaceutically acceptable salt of azelastine is present in the pharmaceutical composition in an amount in the range of about 1 mg to about 10 mg.

Aspect 3 is the pharmaceutical composition of Aspect 1 or 2 wherein the melatonin is present in the pharmaceutical composition in an amount in the range of about 2 mg to about 20 mg.

Aspect 4 is the pharmaceutical composition of any of Aspects 1-3, wherein the melatonin is present in the pharmaceutical composition in an amount in the range of about 2 mg to about 20 mg.

Aspect 5 is the pharmaceutical composition of any of Aspects 1-4, wherein: the azelastine or the pharmaceutically acceptable salt of azelastine is present in the pharmaceutical composition in an amount in the range of about 1 mg to about 10 mg; and the melatonin is present in the pharmaceutical composition in an amount in the range of about 5 mg to about 20 mg.

Aspect 6 is the pharmaceutical composition of any of Aspects 1-5, wherein the pharmaceutically acceptable salt of azelastine is azelastine hydrochloride.

Aspect 7 is the pharmaceutical composition of any of Aspects 1-6, wherein the pharmaceutically acceptable salt of azelastine is azelastine hydrochloride.

Aspect 8 is the pharmaceutical composition of any of Aspects 1-7, wherein the pharmaceutically acceptable salt of azelastine is azelastine hydrochloride, which is present in the pharmaceutical composition and is present in an amount of up to about 10 mg.

Aspect 9 is the pharmaceutical composition of any of Aspects 1-8, wherein the azelastine hydrochloride is present in an amount in the range of about 1 mg to about 10 mg.

Aspect 10 is the pharmaceutical composition of any of Aspects 1-9, wherein the pharmaceutical composition is formulated as an oral pharmaceutical dosage form.

Aspect 11 is the pharmaceutical composition of any of Aspects 1-10, wherein the oral pharmaceutical dosage form is a solid form or a liquid form.

Aspect 12 is a method comprising: administering a pharmaceutical composition to a patient having insomnia or symptoms thereof; wherein the pharmaceutical composition comprises azelastine or a pharmaceutically acceptable salt of azelastine and melatonin.

Aspect 13 is the method of Aspect 12, wherein the pharmaceutical composition is administered once or twice a day, or once every 2 or 3 or 4 days to the patient in an oral solid or liquid form.

Aspect 14 is the method Aspect 12 or 13, wherein the azelastine or the pharmaceutically acceptable salt of azelastine is present in the pharmaceutical composition in an amount in the range of about 1 mg to about 10 mg.

Aspect 15 is the method of any of Aspects 12-14, wherein the melatonin is present in the pharmaceutical composition in an amount in the range of about 2 mg to about 20 mg.

Aspect 16 is the method of any of Aspects 12-15, wherein the melatonin is present in the pharmaceutical composition in an amount in the range of about 2 mg to about 20 mg.

Aspect 17 is the method of any of Aspects 12-16, wherein the azelastine or the pharmaceutically acceptable salt of azelastine is present in the pharmaceutical composition in an amount in the range of about 4 mg to about 10 mg.

Aspect 18 is the method of any of Aspects 12-17, wherein the azelastine or the pharmaceutically acceptable salt of azelastine and the melatonin are present in the pharmaceutical composition in synergistically effective amounts.

Aspect 19 is the method any of Aspects 1-18, wherein the pharmaceutical composition is administered to the patient for a period of up to 8 weeks.

Aspect 20 is the method of any of Aspects 1-19, wherein the pharmaceutical composition is administered to the patient for a period of at least 4 weeks.

Aspect 21 is use of a pharmaceutical composition in the preparation of a medicament for treating a patient having insomnia or one or more symptom thereof, wherein the pharmaceutical composition comprises the composition of any of aspects 1-11, and/or the use involves any of the methods or method steps of aspects 12-20.

Aspect 22 is a pharmaceutical composition for use in treating insomnia or one or more symptom thereof, wherein the pharmaceutical comprises the composition of any of aspects 1-11 and/or the use involves any of the methods or method steps of aspects 12-20.

DETAILED DESCRIPTION OF THE INVENTION

Through clinical practice, the inventors of the present invention found that a pharmaceutical composition with oral dosage forms comprising the active agents, a salt form of azelastine and melatonin, is suitable for treating patients suffering from insomnia and/or symptoms thereof, such as difficulty falling asleep, waking up during the night, waking up too early, daytime tiredness/sleepiness, etc.

The present application is related by subject matter to International Patent Application Nos. PCT/US19/27293, PCT/US19/29885, PCT/US19/33359, PCT/US20/34735, PCT/US20/39916, PCT/US20/59846, and PCT/US21/44654, each of which are hereby incorporated by reference herein in their entireties.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

As used herein, the term "melatonin" refers to N-acetyl-5-methoxy tryptamine.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the solid oral dosage forms are to the amounts and dosage ranges of azelastine hydrochloride.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be by way of any one or more of capsule, tablet, gel, spray, drops, solution, suspensions, syrups, or the like.

The term "about" used herein in the context of quantitative measurements means the indicated amount ±10%. For example, with a ±10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration, for example, admixed with any one or more of conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the pharmaceutical composition with a pharmaceutical diluent which is inert and inserting this mixture into a hard gelatin capsule having the appropriate size. If soft capsules are desired, a slurry of the pharmaceutical composition with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or other non-nutritive sweetener, and/or a biological sweetener and/or a flavoring agent, such as in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure can be typically administered orally. This disclosure therefore provides pharmaceutical compositions that comprise a solid dispersion comprising azelastine and melatonin as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical compositions may further comprise pharmaceutical excipients such as diluents, binders, fillers, glidants, disintegrants, lubricants, solubilizers, and combinations thereof. Some examples of suitable excipients are described herein. When the pharmaceutical compositions are formulated into tablets, tablets may be uncoated or may be coated by known techniques including microencapsulation to delay disintegration and absorption in the gastrointestinal tract and thereby provide a sustained action over a longer period. For example, a time delay material such as glyceryl monostearate or glyceryl distearate alone or with a wax may be employed. In embodiments, the pharmaceutical compositions are formulated as tablets, caplets, pills, or capsules for gastrointestinal absorption, such as formulated to be capable of delaying disintegration until the pharmaceutical composition is in the gastrointestinal tract of a patient. In embodiments, delaying disintegration is achieved using a coating.

In embodiments, the pharmaceutical compositions can comprise synergistically effective amounts of azelastine and melatonin, such as a) about 1 mg to 10 mg of azelastine HCl (or other salt thereof) and b) about 2 mg to 20 mg of melatonin or a) about 2 mg to 6 mg of azelastine HCl (or other salt thereof) and b) about 4 mg to 10 mg of melatonin or a) about 2 mg to 4 mg of azelastine HCl (or other salt thereof) and b) about 4 mg to 6 mg of melatonin, or any amount of azelastine or melatonin within these ranges. In embodiments, the melatonin is present in the pharmaceutical composition in a synergistically effective amount relative to the amount of azelastine or the pharmaceutically acceptable salt of azelastine and can include pharmaceutical compositions comprising a) about up to and including any of 1 mg, 2 mg, 3 mg, 4 mg, 5 mg, 6 mg, 7 mg 8 mg, 9 mg, or 10 mg azelastine, such as azelastine HCl, or any amount within any of these ranges and b) about up to and including any of between 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg melatonin, or any amount within any of these ranges. For example, the compositions comprising synergistically effective amounts of melatonin and azelastine can comprise a) about 4 mg of azelastine HCl and b) about 6 mg of melatonin. Further, for example, compositions of the invention can comprise azelastine or a pharmaceutically acceptable salt of azelastine present in an amount in the range of about 2 mg to about 10 mg and a synergistically effective amount of melatonin in an amount in the range of about 2 mg to about 20 mg. In embodiments, the synergistically effective amounts can be such that the amount of azelastine HCl (or other salt thereof) present in the composition can be equal to, more than, or less than the amount of melatonin present in the composition. In embodiments, the synergistically effective amounts are such that the azelastine is present in the pharmaceutical composition in an amount of at least 1 mg and melatonin is present in an amount of at least 0.1 mg. In embodiments, the synergistically effective amounts can be such that the amount of azelastine HCl (and/or other salt thereof) present in the composition can be the same as, or 2 times as much, or 3 times as much, or 4, 5, 6, 7, 8, 9, 10, 15, 20, 25, 30, 35, 10, 15, or 50 times as much as the amount of melatonin present in the composition, or vice versa. Any one or more of the compositions of the invention can be used with any one or more the methods of the invention disclosed herein, or other methods of using the compositions.

It will be understood, that the amount of the pharmaceutical composition containing azelastine HCl and melatonin actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing azelastine, such as azelastine HCl, and melatonin as described herein are administered to a patient suffering from insomnia, by administration (such as oral administration) once daily, twice daily, up to four times a day, once every other day, once a week, two times a week, three times a week, four times a week, or five times a week, or combinations thereof.

In embodiments, patients are administered the pharmaceutical composition(s) with a therapeutic effective daily dosage of azelastine (such as azelastine HCl) in the range of about 1 mg to about 10 mg and melatonin in an amount in the range of about 2 mg to about 10 mg.

In embodiments, the pharmaceutical dosage forms and tablets of pharmaceutical compositions containing azelastine, such as azelastine HCl, and melatonin as described herein are effective in reversing, reducing, alleviating, and/or treating insomnia in about 1-8 weeks, such as within 1, 2, 3, 4, 5, 6, 7, or 8 weeks, or any range in between.

The following Examples are illustrative and should not be interpreted to limit the scope of the claimed subject matter.

Example 1

A 61-year-old female patient had chronic insomnia for more than 18 months with symptoms including difficulty in falling asleep and two to three awakenings during the sleep period. She tried OTC antihistamine sleeping pills for 3 days, and then melatonin (10 mg daily) for 3 days and they were ineffective in the treatment of her insomnia. She was treated with antidepressant trazodone and later with doxepin, but her insomnia still persisted. After she was provided with eszopiclone, her insomnia was eliminated after initial treatments, but she could not tolerate the side effect of headaches caused by eszopiclone and her insomnia returned after she stopped taking eszopiclone. Then she was provided with a combination of synergistically effective amounts of azelastine (4 mg daily) and melatonin (6 mg daily). With this treatment, the combination of azelastine and melatonin had a synergistic effect, and her insomnia disappeared after the 3rd day of the treatment, whereas melatonin alone was ineffective for her insomnia. This treatment regimen lasted for 8 weeks and she experienced no side effects except a mild metallic taste, and her insomnia has not returned.

Example 2

A 52-year-old female patient had chronic insomnia for more than 6 months. She had difficulty of falling asleep and slept for less than 4 hours every night. She tried melatonin (10 mg daily) as an initial treatment but had no success. She was prescribed with eszopiclone and her sleeping time increased to around 6 hours, but she experienced dizziness and nausea during the daytime after 2 weeks of treatment and she had to stop taking eszopiclone. Then after a week of taking no eszopiclone, she started to experience insomnia again. She was provided with the combination of synergistically effective amounts of azelastine (4 mg) with melatonin (6 mg), daily. With this treatment, the combination of azelastine and melatonin had a synergistic effect, and she can sleep for 6-7 hours daily, whereas with melatonin alone there was no success. With experiencing only bitter taste, this patient has been very satisfied with this treatment.

Example 3

A 47-year-old male patient had chronic insomnia for more than 4 months. He had difficulty falling asleep and slept for 5 to 6 hours every night which caused sleepiness during the daytime and very often prevented him from carrying out his regular tasks at work. Over a period of 3 months, to treat his insomnia, he took diazepam for 7 days, and then zolpidem for 7 days, and then eszopiclone for 2 weeks but he could not tolerate these treatments because of the side effects of drowsiness, dizziness and headache because those side effects prevented him from carrying out his regular task at work as his insomnia did. He was provided with the combination of azelastine (6 mg daily) with melatonin (6 mg daily). After three days of the treatment he could sleep for 6-7 hours a day and experienced no drowsiness, dizziness or headache during the day. He was on the treatment for 6 weeks with no complaints of intolerable side effects.

REFERENCES

A. Menendez Pelaez, and R. J. Reiter, "Distribution of melatonin in mammalian tissues: The relative importance of nuclear versus cytosolic localization". J. Pineal Res. 1993, 15: 59-69.

F. Auld, F., E. Le Maschauer, et al., "Evidence for the efficacy of melatonin in the treatment of primary adult sleep disorders". Sleep Med. Rev. 2017, 34: 10-22.

R. Hardeland, "Neurobiology, pathophysiology, and treatment of melatonin deficiency and dysfunction". The Scientific World Journal 2012, Article ID 640389.

D. Acuna-Castroviejo, G. Escames, et al. "Melatonin role in the mitochondrial function". Frontiers in Bioscience. 2007 12: 947-963.

C. D. Acuna, L. C. Lopez, et al, "Melatonin-mitochondria interplay in health and disease". Current Topics in Med. Chem. 2011, 11: 221-240.

R. J. Reiter, D. X. Tan, and A. Galano, "Melatonin: Exceeding expectations". Physiology 2014, 29: 325-333.

G. Patki and Y. S. Lau, "Melatonin protects against neurobehavioral and mitochondrial deficits in a chronic mouse model of Parkinson's disease". Pharmacol. Biochem. Behav. 2011, 99: 704-711.

R. J. Reiter, J. C. Mayo, et al., "Melatonin as an antioxidant: Under promises but over delivers". J. Pineal Res. 2016, 61: 253-278.

Wei-jie Lv, C. Liu et al, "Melatonin Alleviates Neuroinflammation and Metabolic Disorder in DSS-Induced Depression Rats". Oxidative Medicine and Cellular Longevity 2020, Article ID 1241894.

Monica de la Peña Bravo, L. D. Serpero, et al, "Inflammatory proteins in patients with obstructive sleep apnea with and without daytime sleepiness". Sleep Breath, 2007 September; 11(3):177-85.

R. Nadeem, J. Molnar, et al., Serum inflammatory markers in obstructive sleep apnea: a meta-analysis, Journal of Clinic Sleep Med (2013) October 15; 9(10):1003-12.

J. Gaines, A. N. Vgontzas, et al, "Inflammation mediates the association between visceral adiposity and obstructive sleep apnea in adolescents" Am J. Physiol. Endocrinol Metab., 2016 Nov. 1; 311(5).

Patricia B Williams, Elizabeth Crandall and John D Sheppard, 2010, Azelastine hydrochloride, a dual-acting anti-inflammatory ophthalmic solution, for treatment of allergic conjunctivitis. Clinical Ophthalmology 2010:4 993-1001.

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

Aiko Hatakeyama, 2008, Azelastine hydrochloride on behavioral and psychological symptoms and activities of daily living in dementia patients. Geriatr Gerontol Int 2008; 8: 59-61.

Duraisamy Kempuraj, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.

Kazunori Yoneda, et al. 1997, Suppression by Azelastine Hydrochloride of NF-KB Activation Involved in Generation of Cytokines and Nitric Oxide. Japanese Journal of Pharmacology, 73: 145-53.

Loyd Allen, Ansel's Pharmaceutical Dosage Forms and Drug Delivery Systems, Tenth (2013).

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A pharmaceutical composition, comprising:
   4 mg of azelastine or of a pharmaceutically acceptable salt of azelastine;
   6 mg melatonin;
   and one or more pharmaceutically acceptable excipients.

* * * * *